United States Patent [19]

Tillander

[11] 3,944,916
[45] Mar. 16, 1976

[54] MOISTURE INDICATING PLANT RECEPTACLE

[76] Inventor: Thomas Tillander, 1274 Ryder St., Brooklyn, N.Y. 11234

[22] Filed: Mar. 29, 1974

[21] Appl. No.: 456,230

[52] U.S. Cl. ............... 324/65 P; 47/1.3; 200/61.05; 239/63; 307/118; 340/235
[51] Int. Cl.² .......................................... G01R 27/02
[58] Field of Search ............... 324/65 P, 65 R, 30 B; 340/235; 307/118; 200/61.05, 61.04; 239/63; 47/1.3

[56] References Cited
UNITED STATES PATENTS

| | | | |
|---|---|---|---|
| 882,699 | 3/1908 | Latshaw | 47/1.3 UX |
| 2,171,329 | 8/1939 | Boone | 340/235 |
| 2,468,972 | 5/1949 | Hagerty | 324/65 P |
| 2,611,643 | 9/1952 | Higgins | 324/65 R X |
| 2,721,101 | 10/1955 | Richard, Jr. | 324/65 R X |
| 2,824,282 | 2/1958 | Posey | 324/65 R |
| 2,949,551 | 8/1960 | Sturgeon | 324/65 P |
| 2,968,688 | 1/1961 | Skinner | 340/235 X |
| 3,180,144 | 4/1965 | Bennett | 324/65 P |
| 3,536,999 | 10/1970 | Mandler et al. | 324/65 R |
| 3,601,693 | 8/1971 | Lorentzen | 324/30 B |

*Primary Examiner*—Stanley T. Krawczewicz
*Attorney, Agent, or Firm*—Arthur L. Plevy

[57] ABSTRACT

Apparatus for determining in-situ the moisture content of potting soil in a plant receptacle. A pair of metallic electrodes are positioned on opposite sides of a plant receptacle adjacent the interior wall thereof and at a distance from the top of the receptacle which corresponds to the normal root depth of a plant to be contained therein. Each electrode extends externally of the receptacle for electrical connection to one probe lead or terminal of a resistance meter. When a plant is potted with soil in the receptacle, the resistance measured between the terminals is related to the moisture content of the potting soil.

9 Claims, 9 Drawing Figures

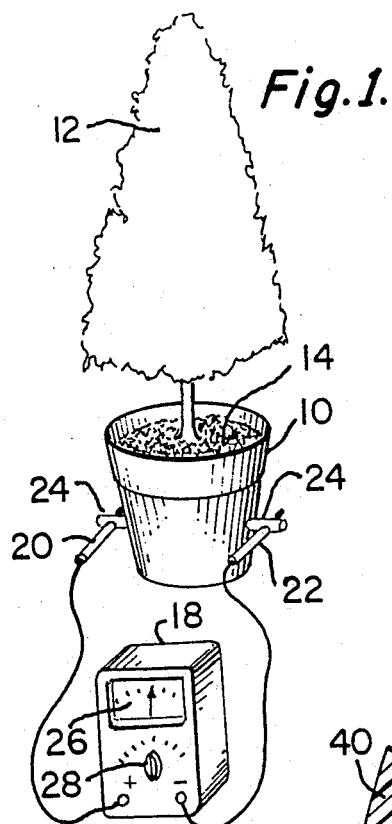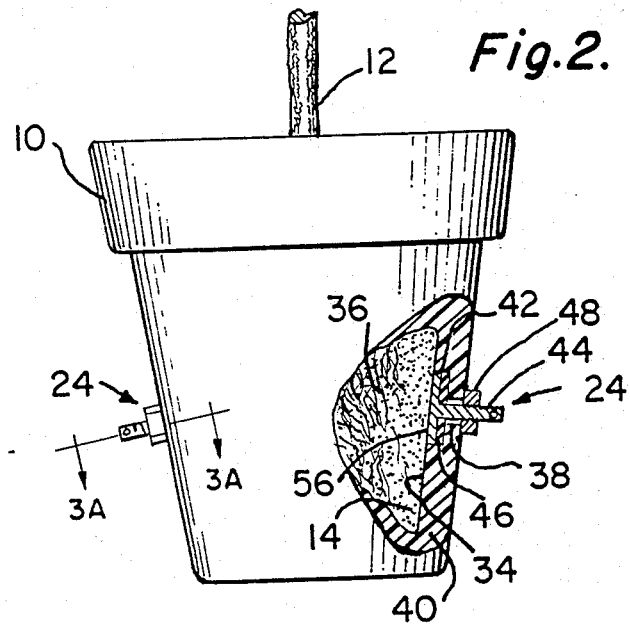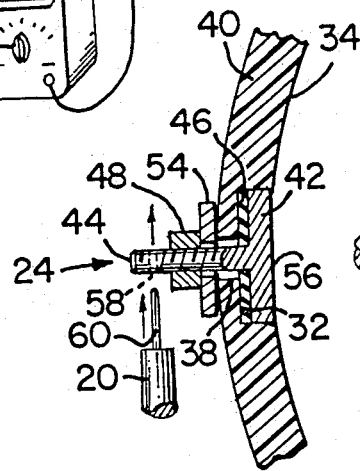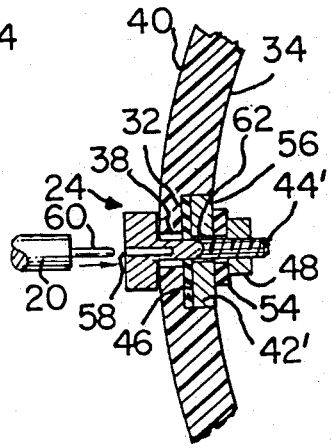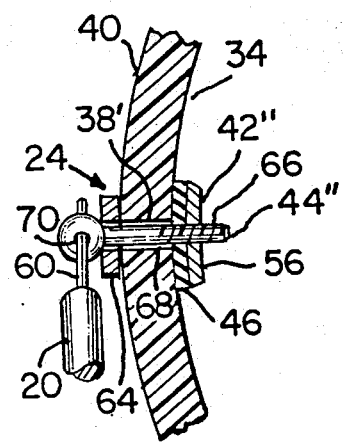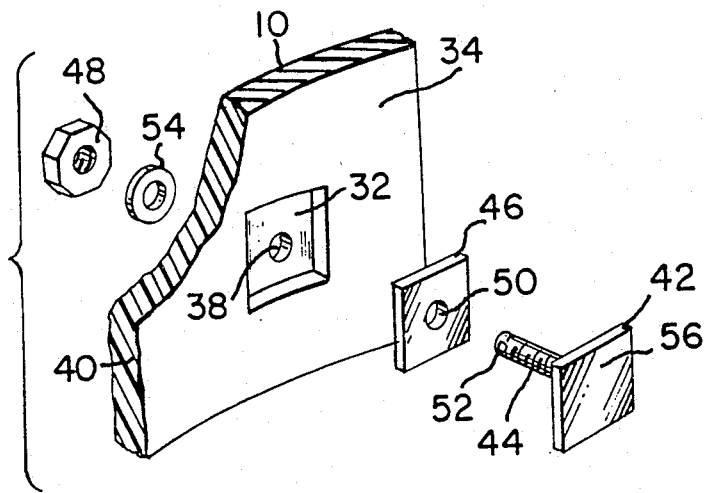

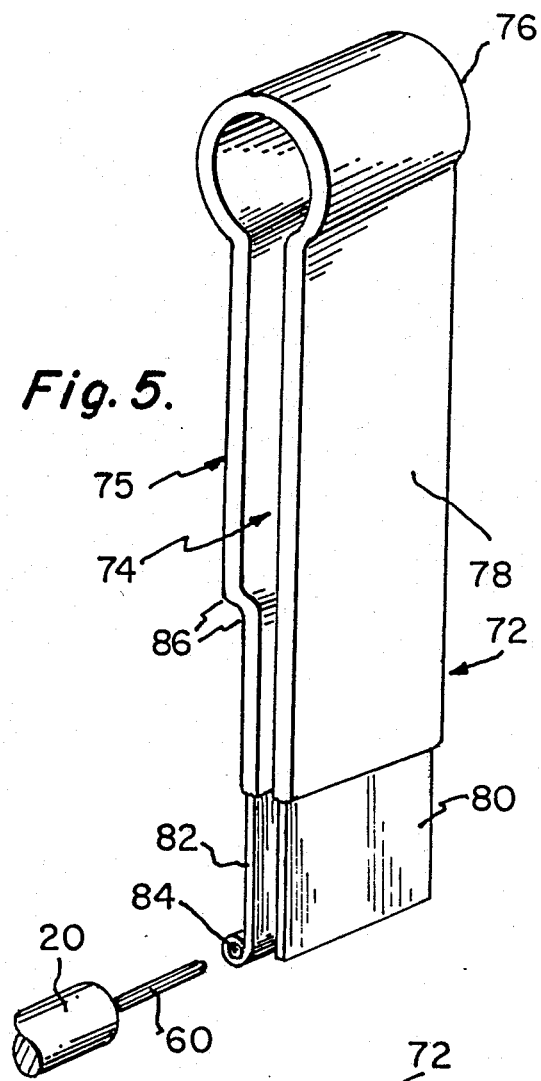
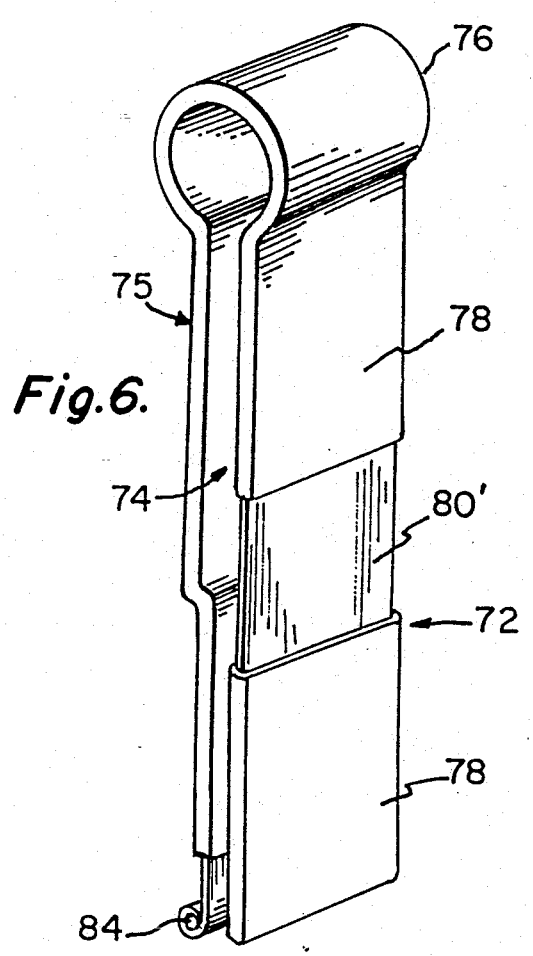
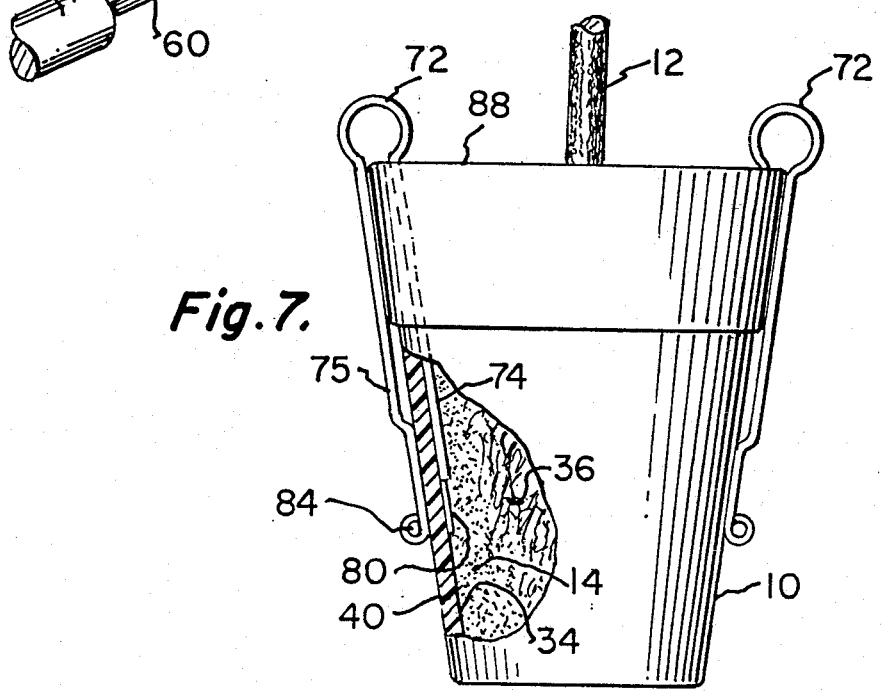

MOISTURE INDICATING PLANT RECEPTACLE

BACKGROUND OF THE INVENTION

This invention relates to plant husbandry and more particularly to a plant receptacle with in-situ means for determining the moisture content of the potting soil therein.

In the husbandry of living plants cultivated in other than a natural environment, such as in greenhouses, nurseries and private homes, it is necessary that the moisture content of the soil in which the plants are growing be maintained at an optimum level to prevent plant loss or retardation of growth. Household plants are especially susceptible to such misfortunes in that the home environment is even less compatible with a natural environment than that of a greenhouse or nursery. Amateur home horticulturists are not always aware that optimum soil moisture content varies with the plant species and are not always knowledgeable of the optimum soil moisture content for the particular plant species they wish to cultivate. Widely diseminating such knowledge, however, is not a solution to the problem unless a simple, economical device for measuring the moisture content of soil is available.

It is known that the approximate moisture content of soil may be ascertained by measuring the resistance between two spaced points in the soil and comparing the resistance measured with the resistance of similar soil having a known moisture content. One example is found in U.S. Pat. No. 2,461,111 which shows a moisture indicating apparatus having two spaced stakes, each of which has an electrode attached thereto and electrically connected to an ohmmeter. The stakes are thrust into the soil to a known depth and the soil resistance is measured and evaluated in terms of soil moisture content. This apparatus is primarily useful, however, in the cultivation of fruits and vegetables in an outdoor environment. It has also been suggested that plant moisture meters having a single probe be used by inserting the probe into the soil of a house plant. The problems encountered by the use of such a meter is that the moisture being measured at a particular point is not representative of the soil conditions across the roots of the plant. A disadvantage of using the frequency apparatus to measure the moisture content of the soil in a plant receptacle is the possbility of damaging delicate root structure when the stakes are frequently thrust into the potting soil.

SUMMARY OF THE INVENTION

The present invention is a novel plant receptacle for use with a resistance meter to enable the in-situ determination of the moisture content of the potting soil at root depth of a plant contained therein. A pair of flat metallic electrodes are at opposite points adjacent the inner wall of the plant receptacle, which may be a standard clay or plastic receptacle. In one embodiment of the invention, a metallic terminal, electrically connected to each electrode, penetrates the wall of the receptacle. Alternatively, the electrode and terminal may be a removable slip-on or clip-type metallic member having two adjacent elongated prongs insulated over a portion of their length. When installed on the plant receptacle, one prong of the member extends along the interior wall of the receptacle in intimate contact with the potting soil therein, the other prong extends along the exterior receptacle wall.

According to the present invention, a pair of in-situ electrodes are permanently or semi-permanently attached to a plant receptacle to provide spaced points across which the moisture content of the potting soil at root depth may be conveniently and quickly determined without danger of injury to the delicate root structure of a plant contained in the receptacle. While not limited thereto, the invention is particularly applicable to plant receptacles such as flower pots, shaped generally in the form of an inverted conical frustrun.

A feature of the invention is the construction of the externally extending electrode of the plant receptacle which is preferably provided with an aperture in which a probe or lead terminal of a meter may expeditiously be inserted to rest therein and make electrical contact with the electrode without the need for a clamp to engage the electrode. By using such a feature, one is able to quickly measure the moisture content of the soils in a large number of plant receptacles in a minimum amount of time.

The availability in recent years of inexpensive solid-state resistance meters makes it feasible for even individuals of modest financial resources to use the present invention to practice more effective plant husbandry then heretofore possible.

OBJECTS OF THE INVENTION

An object of the invention is to enable the in-situ determination of approximate soil moisture content in a plant receptacle at the root depth of a plant contained therein without injury to the roots of the plant.

Another object of the present invention is to permit the convenient, inexpensive and rapid day-to-day measurement of the approximate moisture content of the potting soil in a number of plant receptacles.

Still another object of the invention is the provision of a plant receptacle having relatively unobtrusive electrodes and terminals for measuring the resistance of the soil therein so as to avoid detracting from the appearance of the plant contained in the receptacle.

Other objects, advantages and novel features of the invention will appear from a reading of the following detailed description of the invention when considered in conjunction with the accompanying drawings.

BRIEF DESCRIPTION OF THE DRAWINGS

FIG. 1 is a perspective view of a resistance meter connected across the termianls of a plant receptacle embodying the present invention.

FIG. 2 is a front elevation view of a plant receptacle with a broken away section showing an embodiment of the present invention.

FIGS. 3A through 3C are detailed cross-sectional views taken in the plane 3—3 of FIG. 2 showing alternative arrangements of the electrode assembly of the invention.

FIG. 4 is an exploded view in perspective of a section of a plant receptacle showing an electrode assembly.

FIG. 5 is a perspective view of a slip-on or clip-type electrode of the invention.

FIG. 6 is a perspective view of a modification of the slip-on or clip-type electrode of FIG. 5.

FIG. 7 is a front elevation view of a plant receptacle with a broken away section showing the manner of attachment of the slip-on or clip-type electrode of FIG. 5.

DETAILED DESCRIPTION OF THE INVENTION

Referring now in detail to the drawings wherein like reference characters represent like parts throughout the several views and equivalent parts are disignated by prime symbols.

FIG. 1 illustrates a plant 12 potted with potting soil 14 in plant receptacle 10 which is shown as a standard clay pot but may be any form of plant container. The electrical resistance of potting soil 14 may be previously determined for a given electrode area, electrode spacing and moisture content. Positive and negative probes 20, 22 respectively of resistance meter 18 are inserted in a pair of identical diametrically opposite electrode assemblies 24 extending from the interior of receptacle 10. Electrode assemblies 24 will be more fully described hereinafter. The resistance across electrode assemblies 24 is measured by observing meter 26 which has been set to the proper scale using knob 28. It will be understood that meter 26 may be appropriately marked in any convenient manner to permit a direct reading of soil moisture content for a given soil, electrode area and electrode spacing.

FIGS. 2, 3A and 4 show in greater detail one electrode assembly 22 installed in the plant receptacle of the present invention. For convenience and clarity of description the arrangement of only a single electrode assembly 24 will be described. The plant receptacle 10 is provided with a recess or indent 32 positioned on the interior surface 34 thereof at a depth in the receptacle 10 commensurate with the normal depth of the roots 36 of a plant 12 contained therein. The electrodes may be positioned half way down from the top edge of the pot receptacle even though the plant roots may extend down to the bottom of the receptacle. An opening 38 centrally positioned in the recess 32 extends radially through the wall 40 of the receptacle 10. A sealing gasket 46 having a central opening 50 there through is located in the recess 32. The gasket 46 may be made of rubber, neoprene or other resilient sealing material.

A flat metallic electrode 42 having a threaded metallic shaft 44 centrally affixed to one side thereof is inserted in the recess 32. Shaft 44 extends through opening 50 in the gasket 46 and opening 38 in wall 40. A threaded nut 48 and a washer 54 are provided on shaft 44 to urge electrode 42 against gasket 46 sufficiently to form a watertight seal between the electrode 42 and the flat surface of recess 32. As shown best in FIG. 4 the electrode 42, gasket 46 and recess 32 are generally square in configuration but may be rectangular, circular or other shapes without departing from the scope of the invention.

The front surface 56 of the electrode 42 is approximately flush with the interior surface 34 of the receptacle 10 and is in intimate contact with potting soil 14. The flush surface enables soil to be packed down in the receptacle without soil catching on the top edge of the plate 56 and creating air holes in the soil at the top and bottom edges of plate 56 which may interfere with proper measurement of the moisture content of the soil. Preferably, electrode 42 is made of a relatively non-corrosive metal such as aluminum or copper.

A hole 58 is located in the outwardly projecting end of threaded shaft 44 transverse to its longitudinal axis. As shown in FIG. 3B, however, hole 58 may be located at the end of shaft 44 concentric with its longitudinal axis. The diameter of hole 58 is dimensioned to slidingly receive and made electrical contact with the metallic tip 60 of terminal probe 20 of a meter in order to free the hands of an operator for manipulation of the knob 28 of resistance meter 18.

In FIG. 3B an alternative embodiment of the electrode assembly 24 is illustrated. A threaded bolt 44' is inserted through hole 38 in wall 40, through hole 50 in gasket 46, thence through hole 62 in electrode 42'. A washer 54 and threaded nut 48 are provided on the inwardly projecting end of bolt 44' to urge electrode 42' against gasket 46 to form a watertight seal between the electrode 42' and recess 32. To insure the watertight integrity of the electrode assembly 24, the annular space between bolt 44', and hole 62 may be filled with a flexible sealant.

FIG. 3C illustrates another embodiment of the electrode assembly 24 wherein a threaded eye-bolt is inserted inwardly through washer 64, hole 38' in wall 40, hole 50 in gasket 46 and threaded into a centrally located threaded opening 66 in electrode 42''. The eye-bolt 44'' is tightened to urge electrode 42'' against gasket 46 to form a watertight seal between electrode 42'' and the inner surface 34 of receptacle wall 40. The annular space 68 between hole 38' and threaded eye-bolt 44'' may be filled with a flexible sealant to insure watertight integrity.

The electrode 42'' may be arcuate-shaped in one dimension to approximately conform to the curvature of the interior wall 34, and may have tapered edges on all four sides as shown to avoid air holes in the soil. The arrangement of FIG. 3C is especially adapted for use with plant receptacles of wall thicknesses insufficient to form a recess in the inner wall, thereof. To make electrical contact with the resistance meter 18 the metallic tip 60 of terminal probe 20 of the meter is positioned in the eye 70 of eye-bolt 44'' as shown in the figures.

In the embodiments of FIGS. 3A, 3B and 3C the metallic tip need merely be inserted into the elongated aperture or hole 58 or into the opening of eye 70 to rest therein in order to make electrical contact with the electrode assembly without the need for a clamp to attach the meter lead to the electrode assembly. For this purpose, in FIG. 3C eye 70 of eye-bolt 44' should preferably be positioned in the horizontal plane. FIG. 5 shows a slip-on or clip-type electrode 72 adapted for use with standard plant receptacles not provided with an integral electrode assembly. The slip-on electrode comprises a pair of spaced, flat metallic prongs 74,75 are mechanically and electrically joined at their upper ends by a bridging or an arcuate-shaped member 76. The prongs may, however, be formed by bending a single strip of flat metallic stock into the above described shape. The electrode 72 is preferably made of a relatively non-corrosive metal having good spring characteristics such as, for example, certain stainless steels. The clip-type electrode 72 is provided with an insulating coating 78 covering the member 76 and an appreciable portion of the length of prongs 74,75. The lower, unjoined or free ends 80,82 of the metallic prongs 74,75 are uninsulated portions and remain exposed. Portion 80 has a known area for purposes of measuring the soil resistance. Insulating coating material 78 may be attached to the electrode 72 by any suitable means including dip-insulating. The lower end of portion 82 is rolled or curled for the entire width thereof to form an opening or aperture 84 into which the tip 60 of probe 20 may be inserted. The tip 60 makes electrical contact with the interior of opening 84 and is supported thereby.

Prong 75 is provided with two 90° bends 86 at an intermediate portion of its length so as to decrease the spacing between the lower portion of the prongs 74,75, a feature of the invention which will be discussed subsequently.

In FIG. 7, a pair of slip-on or clip-type electrodes 72 are illustrated in diametrically opposite locations on a plant receptacle 10. As is apparent from the figure the electrode 72 has been positioned to straddle the upper edge or lip 88 of receptacle 10 so that prong 74 extends into the receptacle adjacent the inner wall thereof and prong 75 extends along the exterior thereof. Lower portion 80 of prong 74 is in intimate contact with the potting soil 14 contained in the receptacle 10 at a location about one-half way down from the lip 88. The decreased spacing, previously mentioned, between the lower portions of prongs 74,75 provides a clamping force on wall 40 of the receptacle 10 to insure that the portion 80 of the electrode remains substantially closely adjacent to the interior wall surface 34 of the receptacle 10. It should be noted that portion 80 is at a depth in receptacle 10 commensurate with the depth of the roots 36 of the plant 12.

FIG. 6 shows a modification of the slip-on or clip-type electrode 72 wherein exposed portion 80' of a known area is located at an intermediate portion of prong 74. It will be appreciated that the exposed portion 80' may be positioned along the length of prong 74 so as to vary the depth at which the resistance of potting soil 14 is measured. This feature is particularly useful in practicing the present invention with plant receptacles of varying depths or with various plant species having root structures located at different depths below the surface.

To evaluate the measured resistance of the soil in a particular plant receptacle in terms of moisture content, the resistance of a similar soil of a known moisture content is determined with various electrode spacings for the electrode area utilized. By maintaining a constant electrode area, a reference graph may be prepared for a particular soil relating moisture content to resistance for various electrode spacings.

As can be seen from the foregoing description, the present invention provides a novel plant receptacle for use in day-to-day maintenance of proper soil moisture content for any plant species. Further, the invention eliminates the possibility of injury to delicate root structure.

It is understood that the present invention is not to be limited, for example, by a particular type of plant receptacle, by a particular electrode metal nor by a particular resistance measuring apparatus. Many modifications and variations of the present invention are possible in light of the above teachings and within the purview of the appended claims without departing from the spirit and scope of the invention.

I claim:

1. A plant receptacle for measuring the moisture content of the soil adapted to be contained therein, comprising two spaced metallic electrodes on the interior wall of said receptacle positioned at a depth in said receptacle commensurate with the normal root level of a plant adapted to be potted in said soil, and metallic terminals on the exterior of said receptacle electrically connected to said electrodes, and means coupled to said metallic terminals for indicating the moisture content of said soil at said root level of said plant.

2. A receptacle according to claim 1 wherein the interior wall of said receptacle is provided with two recesses on diametrically opposite locations, said electrodes comprising metallic plates positioned in said recesses.

3. A receptacle according to claim 2 wherein the wall of said receptacle has openings there through at the locations of said recesses, said terminals extending through said openings to the exterior of said receptacle.

4. A receptacle according to claim 3 wherein the exterior ends of said terminals are provided with apertures therein for supporting and making electrical contact with the electrical probes of a resistance meter.

5. A receptacle according to claim 1 wherein said electrodes are slip-on clips positioned on opposite sides of said receptacle each comprising a pair of spaced flat metallic prongs joined at one end and free at the other end, and electrical insulation covering said slip-on clips except for a portion of the length of said prongs, said portion being uninsulated each of said slip-on clips at the joined ends straddling the top edge of said receptacle whereby one prong thereof extends into the interior and close to the wall of said receptacle and the other prong extends externally of said receptacle.

6. A receptacle according to claim 5 wherein the free ends of the externally extending prongs of said clips are rolled to form an aperture in each end for supporting and making electrical contact with the electrical probes of a resistance meter.

7. A receptacle according to claim 5 wherein an intermediate portion of the length of one prong of each slip-on clip is bent inwards to reduce the spacing between the prongs at the free end of said clip.

8. A receptacle according to claim 5 wherein said uninsulated portion of said prongs is located at the free ends thereof.

9. A receptacle according to claim 5 wherein said uninsulated portion of said prongs is located intermediate the length of said prongs.

* * * * *